US007621983B2

(12) United States Patent
Neri

(10) Patent No.: US 7,621,983 B2
(45) Date of Patent: *Nov. 24, 2009

(54) TRANSDUCTION-PROTECTION DEVICE

(75) Inventor: Roberto Neri, Mirandola (IT)

(73) Assignee: Gambro Lundia AB (SE)

( * ) Notice: Subject to any disclaimer, the term of this patent is extended or adjusted under 35 U.S.C. 154(b) by 316 days.

This patent is subject to a terminal disclaimer.

(21) Appl. No.: 11/635,520

(22) Filed: Dec. 8, 2006

(65) Prior Publication Data

US 2007/0084779 A1    Apr. 19, 2007

Related U.S. Application Data

(63) Continuation of application No. 10/804,147, filed on Mar. 19, 2004, now Pat. No. 7,175,697.

(60) Provisional application No. 60/480,403, filed on Jun. 23, 2003.

(30) Foreign Application Priority Data

Mar. 21, 2003   (IT)   .................. MO2003A0079

(51) Int. Cl.
*B01D 53/22* (2006.01)
(52) U.S. Cl. ............................. 96/9; 55/511
(58) Field of Classification Search ............ 96/4, 96/7, 9, 11–14; 95/54, 43; 55/495, 497, 55/502, 511; 600/488; 210/489, 500.21, 210/321.84
See application file for complete search history.

(56) References Cited

U.S. PATENT DOCUMENTS

| | | | |
|---|---|---|---|
| 4,314,480 A | 2/1982 | Becker | |
| 4,493,693 A | 1/1985 | Bilstad et al. | |
| 4,501,663 A * | 2/1985 | Merrill | 210/347 |
| 5,269,917 A * | 12/1993 | Stankowski | 210/232 |
| 5,443,723 A * | 8/1995 | Stankowski et al. | 210/321.75 |
| 5,458,586 A | 10/1995 | Adiletta | |
| 5,500,003 A | 3/1996 | Guala et al. | |
| 5,603,792 A | 2/1997 | Guala et al. | |
| 6,086,762 A | 7/2000 | Guala | |
| 6,168,653 B1 | 1/2001 | Myers | |

(Continued)

FOREIGN PATENT DOCUMENTS

DE    3126850    3/1982

(Continued)

*Primary Examiner*—Frank M Lawrence
(74) *Attorney, Agent, or Firm*—Finnegan, Henderson, Farabow, Garrett & Dunner L.L.P.

(57) ABSTRACT

A transduction-protection device for protecting medical apparatus from contamination by infectious agents comprises a containment body having an inlet destined to be set in fluid communication with an extracorporeal circuit of blood, and an outlet destined to be connected to a fluid line operatively connected to a pressure gauge of a medical apparatus. The inlet is in gas communication with the outlet across an internal cavity of the containment body. Two hydrophobic membranes are predisposed in the containment body between the inlet and the outlet. The membranes each define an anticontamination barrier which is gas-permeable. The device transmits the pressure of the extracorporeal circuit to the pressure gauge, with no relevant loss of head, while at the same time protecting, with a high degree of security, the medical apparatus from risks of contamination by pathogens originating in the extracorporeal circuit.

20 Claims, 13 Drawing Sheets

U.S. PATENT DOCUMENTS

| | | |
|---|---|---|
| 6,506,237 B2 | 1/2003 | Myers |
| 6,536,278 B1 | 3/2003 | Scagliarini |
| 6,602,325 B1 * | 8/2003 | Frost et al. ............ 95/56 |
| 7,004,915 B2 | 2/2006 | Boynton et al. |
| 7,069,788 B2 | 7/2006 | Teugels |
| 2004/0173516 A1 | 9/2004 | Guala |

FOREIGN PATENT DOCUMENTS

| | | |
|---|---|---|
| DE | 19816871 | 10/1999 |
| EP | 0536297 | 4/1993 |
| EP | 0652018 A2 | 5/1995 |
| EP | 0878628 B1 | 11/1998 |
| EP | 0887085 B1 | 12/1998 |
| EP | 1097725 A2 | 5/2001 |
| EP | 1547630 A1 | 6/2005 |
| GB | 2168263 | 6/1986 |
| IT | TO93A000368 | 5/1993 |
| IT | TO96A001000 | 12/1996 |
| JP | 10-505413 | 5/1998 |
| JP | 2002-71494 | 3/2002 |
| WO | WO 96/05494 | 2/1996 |
| WO | WO 99/54022 | 10/1999 |

* cited by examiner

TRANSDUCTION-PROTECTION DEVICE

This application is a continuation of application Ser. No. 10/804,147, now U.S. Pat. No. 7,175,697, filed Mar. 19, 2004, which claims the benefit of priority of Italian Application No. MO2003A000079, filed on Mar. 21, 2003, and claims the benefit of U.S. provisional application no. 60/480,403, filed Jun. 23, 2003, all of which are incorporated herein by reference.

BACKGROUND OF THE INVENTION

The invention relates to a transduction-production device for protecting medical apparatus, in particular from contamination by infectious agents.

Specifically, though not exclusively, the invention can be usefully applied to an apparatus for extracorporeal blood treatment, in particular for treatment of renal insufficiency.

In particular, the invention relates to a transduction-protection device comprising a containing hollow body, having an inlet for communication with an extracorporeal circuit, and an outlet for communication with an operator unit of the medical apparatus, for example with a device for measuring the pressure in the extracorporeal circuit. The device of the operation functions as a transducer, which is both able to transmit pressure from the inlet to the outlet allowing for no drop in pressure and also as an aseptic barrier which protects the medical apparatus from infectious agents originating from the patient.

In more detail, the present invention relates to a device comprising a containing hollow body having an inlet comprising a first tubular connector, destined to be connected to a fluid line associated during operation with an extracorporeal fluid transport circuit, and an outlet comprising a second tubular connector, destined for connection with a fluid line associated during operation to an operator unit of a medical apparatus, the operator unit comprising, for example, a pressure gauge; the first and second tubular connectors being in reciprocal gas communication through an internal cavity of the hollow body, which contains a hydrophobic membrane which defines within the cavity an anti-contamination barrier which is gas-permeable and which is arranged transversally between the first and second tubular connectors.

The device enables transmission of the pressure from the extracorporeal fluid transport circuit to the pressure gauge, without significant losses of head, while at the same time protecting the operators, the medical apparatus, which the pressure gauge is part of, and the surrounding environment, from the risk of contamination from pathogens originating from the fluid running in the extracorporeal circuit. The device can further protect the extracorporeal circuit and therefore the patient too, from intrusion of extraneous particles originating from the medical apparatus.

Transduction-protection devices of the above-described type already exist in the prior art, for example in U.S. Pat. No. 4,314,480, U.S. Pat. No. 5,500,003, U.S. Pat. No. 5,603,792, U.S. Pat. No. 6,086,762, U.S. Pat. No. 6,168,653, U.S. Pat. No. 6,506,237, U.S. Pat. No. 6,536,278, U.S. Pat. Publ. No. US2004/0173516, GB 2 168 263, IT 1 270 858, IT 1 289 726, EP 0652 018, and EP 1 097 725, and are commonly known as "blood catchers" or "transducer-protectors".

One of the drawbacks of the known devices is their poor security level: the protective function of the membrane can be lost due to micro-lesions in the membrane itself, or imperfections, even microscopic, in the seal around the perimeter edge of the membrane, which edge is sealed and lies between two plastic elements bearing the two tubular connectors, along an ultrasonic plastic welding zone which, apart from solidly joining the plastic elements and the membrane, also guarantees the seal.

A known solution to this drawback consists in predisposing, along the fluid line, two devices in series, in reciprocal fluid communication. Thanks to this solution, even if one of the two devices were to fail, the protective function should be guaranteed by the other device. This solution, however, leads to increases in costs, due to the need to realize two distinct ultrasonic welding processes, one for each device, and also due to the need subsequently to realize a connection to the fluid line of the two devices.

SUMMARY OF THE INVENTION

A main aim of the present invention is to provide a device, of the above-described type, which is able to overcome the above-mentioned drawbacks inherent in the prior art.

A further aim of the invention is to make available a simple and economical process for manufacturing the device of the invention.

An advantage of the invention is that it provides a simple and economical device which can guarantee a high degree of security against contamination by infectious agents.

A further advantage of the present invention is that it provides a device which is able to transmit, with extreme ease and reliability, the pressure signal coming from the extracorporeal circuit.

A further advantage is that the invention provides a relatively small device.

These aims and advantages and more besides are all attained by the invention, as it is characterised in one or more of the appended claims.

According to a characteristic of the invention, the hollow body has an intermediate portions, comprised between the two tubular connectors, made in a single piece and having a central opening for passage of gas, to which two hydrophobic membranes are associated, on opposite sides of the intermediate portion and peripherally sealed. Each of the hydrophobic membranes functions as an aseptic barrier against contamination.

This characteristic guarantees protective effectiveness, thanks to the presence of two aseptic barriers arranged in series one following another, in a device which is constructionally simple and economic and of contained size.

In a characteristic of the invention, the intermediate portion is plate-shaped, with an axial dimension that is smaller than its radial dimensions, having a central opening for passage of gas.

This allows the various parts making up the device to be solidly joined together; i.e the three portions of the body and the two hydrophobic membranes, by a single ultrasonic welding operation.

Further characteristics and advantages of the present invention will better emerge from the detailed description which follows, of at least one embodiment of the invention, illustrated non-exclusively by way of example in the accompanying figures of the drawings.

BRIEF DESCRIPTION OF THE DRAWINGS

The description that follows will make reference to the figures of the drawings, provided by way of example and therefore non-limiting, in which.

Figure 23:
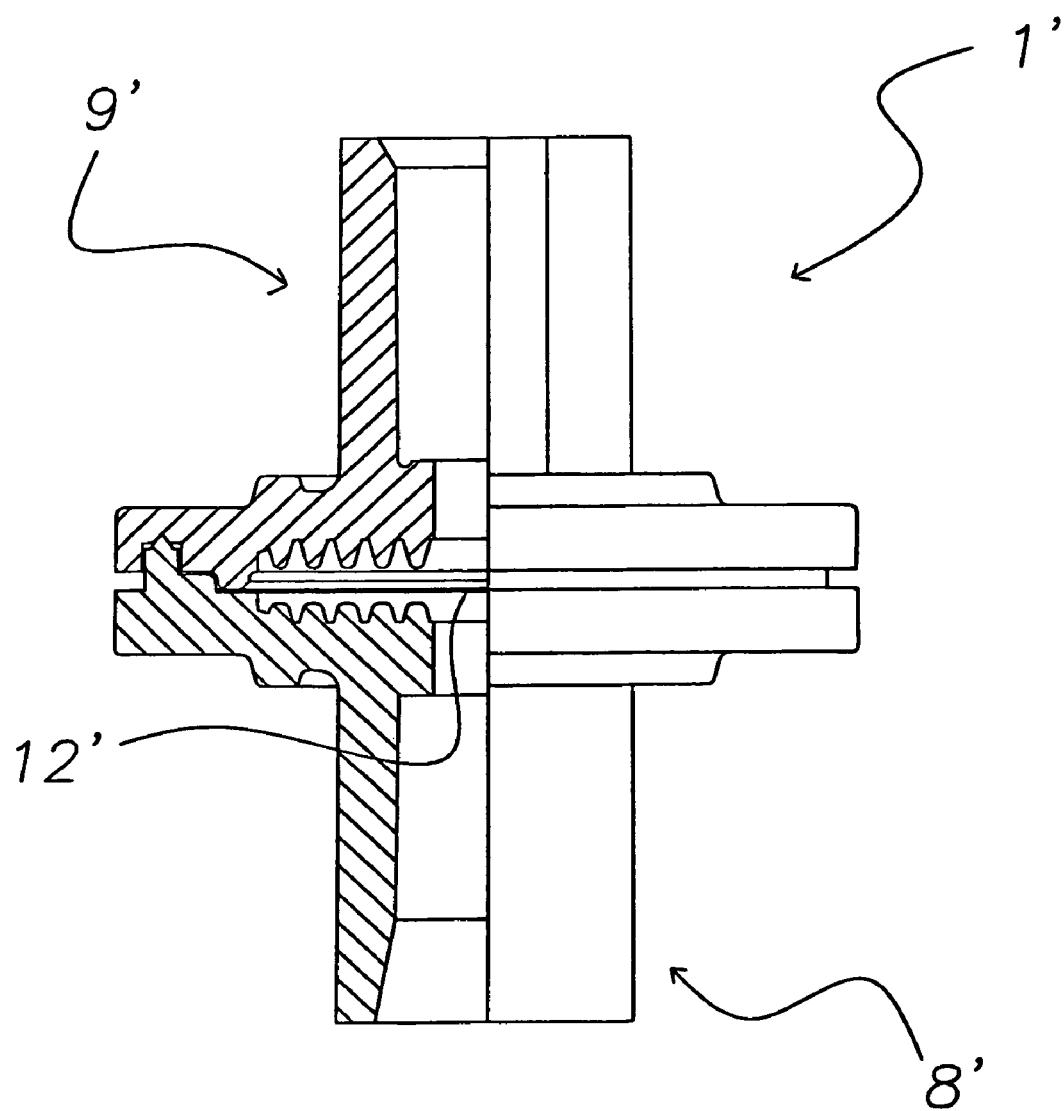

FIGS. from 19 to 22 show four embodiments of the device of the invention with various types of tubular connections;

FIG. 23 is a partially sectioned view of a further embodiment of the present invention.

DETAILED DESCRIPTION 1 denotes in its entirety a device for protecting medical apparatus from contamination by infectious agents. The protection device 1 is used in particular in combination with apparatus for extracorporeal blood treatment, for example in treatment of renal insufficiency (dialysis machines).

The device 1 is predisposed to operate along an auxiliary line 2 which connects an extracorporeal blood circuit 3 with a medical apparatus 4. The device 1 has the double function of protecting and transducing, i.e. of protecting the medical apparatus 4, the operators and the surrounding environment, while at the same time transmitting the extracorporeal circuit 3 pressure to a pressure gauge, known and not illustrated, which is part of the medical apparatus 4, with no significant loss of head.

Figure 2:
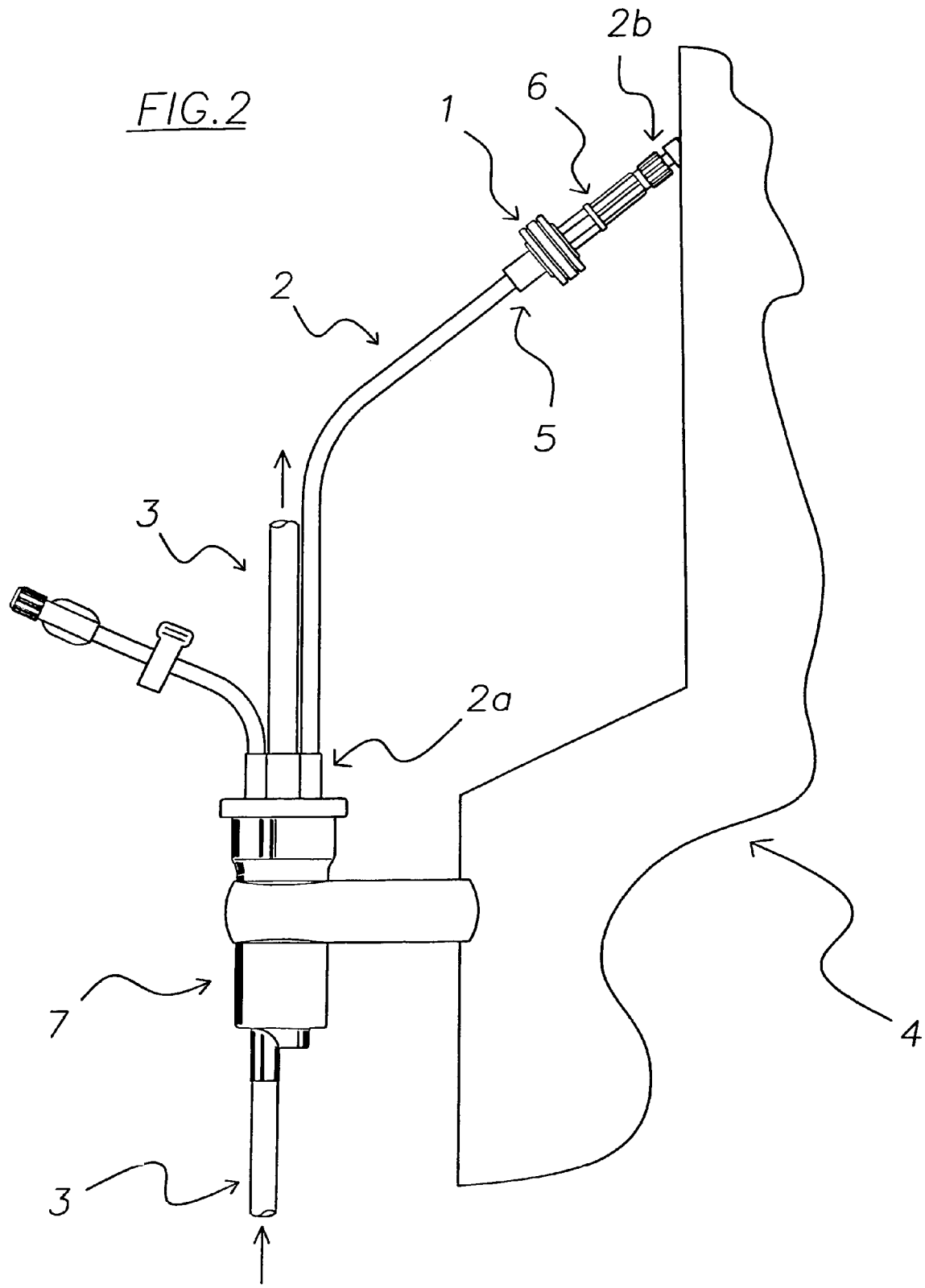
FIG. 2 is a view in vertical elevation of a part of a dialysis apparatus comprising the device of FIG. 1.
Figure 3:
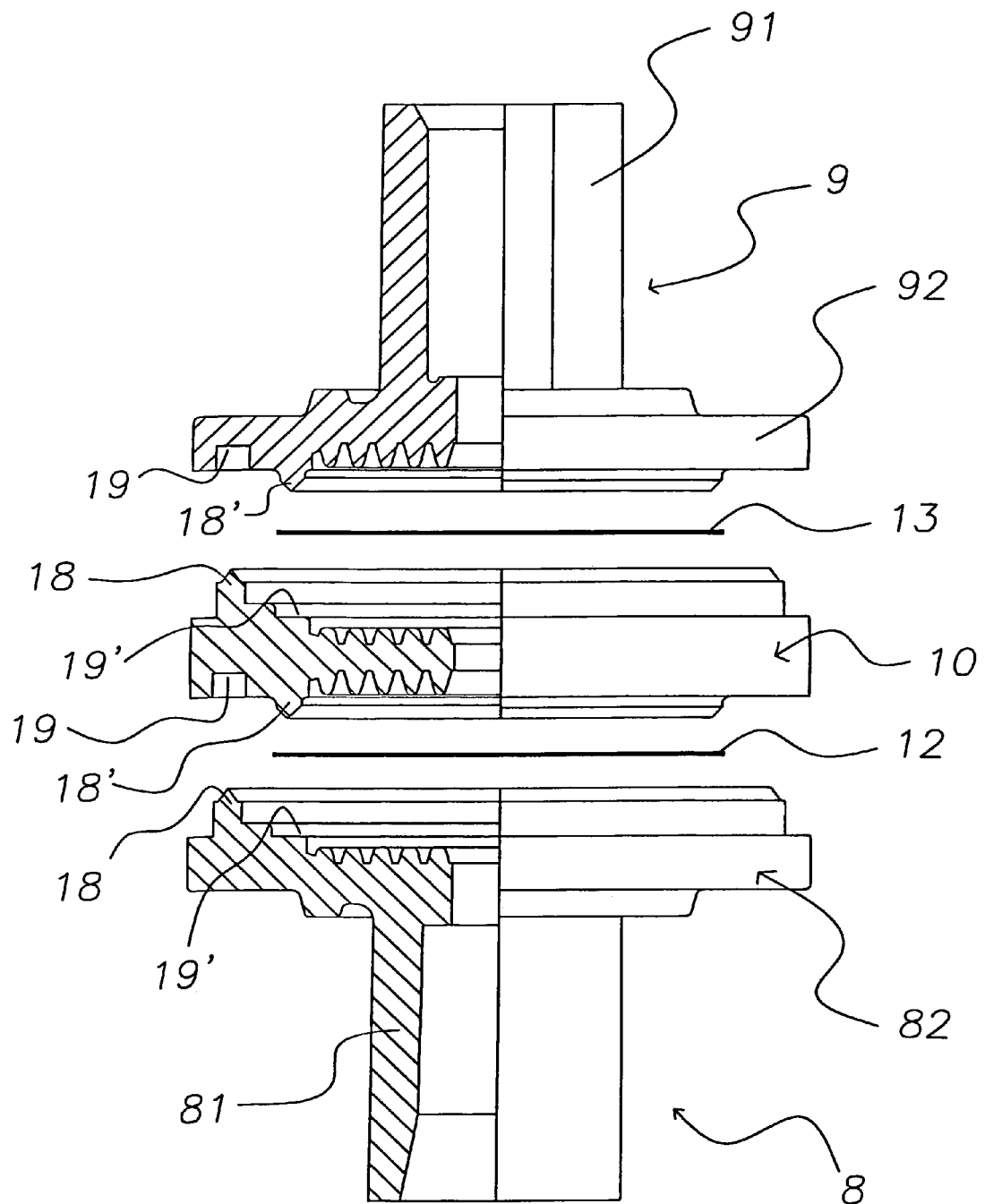
FIG. 3 is the device of FIG. 1 before assembly of the components.

The device 1 comprises a hallow body having an inlet 5 communicating with the extracorporeal blood circuit 3, and an outlet 6, communicating with the medical apparatus 4. The auxiliary line 2, in which the protection device 1 is inserted, has one end, an inlet end 2a, connected to a zone of the extracorporeal circuit 3, and another end, an outlet end 2b, connected to the medical apparatus 4. In more detail, in the embodiment illustrated in FIG. 2, the inlet end 2a of the auxiliary line 2 is attached to a rigid-walled container 7 (for example an arterial chamber of an extracorporeal blood circuit); the outlet end 2b of the auxiliary line 2 is connected to a pressure transducer (not illustrated) which transforms the pressure signal, transmitted through the protection device 1, into a corresponding electric signal which is received by a control unit of the medical apparatus 4. FIG. 2 partially shows a front panel of the medical apparatus 4, which exhibits a seating predisposed for removable connection with an end connector of the auxiliary line 2.

The hollow body comprises a first end portion 8, a second end portion 9 opposite the first end portion 8, and a third intermediate portion 10 interpositioned between the two end portions 8 and 9. Each of the three portions, 8, 9 and 10, is made of a rigid plastic material (in the illustrated embodiment PETG), and is in a single piece and manufactured by plastic moulding.

The first end portion 8 has a first tubular connector 81, which defines the inlet 5 of the hollow body, destined to be connected with a fluid line connected during operation to the extracorporeal fluid transport circuit. In the illustrated embodiment, the fluid line (auxiliary line 2) comprises a flexible tube, made of a plastic material, joined to the first tubular connector 81 by force-fitting and gluing.

The second end portion 9 has a second tubular connector 91, which defines the outlet 6 of the hollow body, and which is in gas communication with the first tubular connector 81 through an internal cavity 11 of the hollow body; the second tubular connector 91 is destined to be connected to a fluid line which during operation is connected to the pressure gauge of the medical apparatus 4. The two tubular connectors 81 and 91 are reciprocally coaxial.

The two end portions 8 and 9 each have a flanged part 82 and 92 which exhibits, as will be better described herein below, at least one permanent join zone with the third intermediate portion 10.

The third intermediate portion 10 is plate-shaped, centrally open, coaxial with the two end portions 8 and 9, and has an axial dimension which is smaller than the radial dimensions thereof.

The central opening of the third intermediate portion 10 allows passage of gas. The third intermediate portion 10 is, in substance, a flanged union element between the two end portions 8 and 9. The axial dimension of the flanged element is about the same size (not more than two or three times bigger) as the axial dimension of the flanged parts 82, 92 of the first and second end portions 8 and 9.

The third intermediate portion 10 is coupled on a first side thereof to the first end portion 8 along an annular union zone 102 and is coupled on a second side thereof, opposite to the first side, to the second end portion 9, along an annular union zone 104. The annular union zones 102 and 104 are permanent coupling zones, and are coaxial one to another and have about the same diameter, and in the illustrated embodiment are constituted by ultrasonic weld zones.

As mentioned above, the third intermediate portion 10 is a press-formed single piece plastic element. The third intermediate portion 10 has a prevalently radially-extending development, rather than axially-extending. In other words, the third intermediate portion 10 is more greatly developed in breadth rather than in length, where for length we intend the direction of the longitudinal axis of the hollow body.

The device comprises a first filter membrane 12, with hydrophobic properties, contained in the hollow body and defining, in the cavity 11 of the hollow body, a first anti-contamination aseptic barrier, arranged transversally between the first end portion 8 and the third intermediate portion 10. A second filter membrane 13 is housed in the hollow body, which second membrane has hydrophobic properties and defines, in the cavity 11 of the hollow body, a second anti-contamination aseptic barrier, arranged transversally between the second end portion 9 and the third intermediate portion 10.

101 and 103 indicate two annular liquid-seal zones, located at two peripheral sealed edges of the filtering membranes 12 and 13. The peripheral sealed edge of the first filter membrane 12 is pressed, at the annular seal zone 101, between the first end portion 8 and the third intermediate portion 10. The peripheral sealed edge of the second filter membrane 13 is pressed, at the annular seal zone 103, between the second end portion 9 and the third intermediate portion 10. The two annular seal zones 101 and 103 are coaxial and have about the same diameter. Further, the annular seal zones, 101 and 103, are coaxial to the annular union zones 102 and 104, and have a smaller diameter than the annular union zones 102 and 104.

Both the first membrane 12 and the second membrane 13 are formed by at least two layers, one an operating filtering layer, made of polytetrafluoroethylene and facing the inlet 5 of the hollow body, and a support layer, made of non-woven polyester and facing the outlet 6 of the hollow body.

Both the first membrane 12 and the second membrane 13 are filter membranes allowing passage of air, so that changes in pressure on one side of each membrane are transmitted to the opposite side, to which a pressure-sensitive device is connected.

In other words, both the first membrane 12 and the second membrane 13 are gas-permeable to enable transmission of a pressure signal through the protection device 1, from the inlet 5 to the outlet 6, i.e. from the extracorporeal circuit 3 to the pressure gauge of the medical apparatus 4, without determining any relevant loss of head; the pressure measured by the medical apparatus 4 thus corresponds to the effective pressure in the extracorporeal circuit 3.

Further, each filter membrane 12 and 13 blocks non-sterile particles and prevents the passage of contaminating agents from one side to the other of the membrane.

The central part of the first membrane 12 faces the central part of the second membrane 13 in a central gas passage zone internally of the hollow body, comprised between the inlet 5 and the outlet 6 of the hollow body.

The first portion of end 8 has an internal surface which faces and is parallel to the first membrane 12 and delimits the internal cavity 11 of the hollow body. The internal surface is arranged perpendicular to the axis of the hollow body and centrally exhibits an opening for fluid passage. A plurality of reliefs 14 are fashioned from the internal surface, which reliefs 14 define a striker surface for the first membrane 12.

The second end portion 9 has an internal surface, facing and parallel to the second membrane 13 and delimiting the cavity 11 internally of the hollow body. The internal surface is perpendicular to the axis of the hollow body and centrally exhibits an opening for fluid passage. A plurality of reliefs 15 are fashioned from this surface and define a striker surface for the second membrane 13.

The third intermediate portion 10 has, on two opposite sides, two internal surfaces which delimit the internal cavity 11 of the hollow body, each of which is perpendicular to the axis of the hollow body and centrally exhibits an opening for fluid passage. A plurality of reliefs 16 is fashioned from a first internal surface, facing and parallel to the first membrane 12 on an opposite side thereof with respect to the internal surface of the first end portion 8. The plurality of reliefs 16 defines a striker surface for the first membrane 12. A further plurality of reliefs 17 are fashioned from a second internal surface, opposite to the first internal surface and facing and parallel to the second membrane 13, on an opposite side to the internal surface of the second end portion 9. The plurality of reliefs 17 define a striker surface for the second membrane 13.

The above-cited pluralities of reliefs 14, 15, 16 and 17, fashioned on each of the three portions 8, 9 and 10 of the hollow body, are fashioned as ribs arranged tangentially, with reference to the longitudinal axis of the hollow body, to define a plurality of tangential channels communicating with a central zone of the cavity 11 of the hollow body, through one or more radial channels defined by the reliefs (as can be seen in FIGS. 5, 9, 13 and 16).

The above-mentioned annular liquid-seal zones 101 and 103, which guarantee the aseptic barrier provided by each membrane 12 and 13, are also zones where the peripheral edges of the membranes 12 and 13, squeezed between the first end portion 8 and the third intermediate portion 10, and the third intermediate portion 10 and the second end portion 9—are solidly constrained to the hollow body.

The described device is manufactured using a process which includes a preliminary stage of preparation, by means of plastic press-forming, of the three portions 8, 9 and 10 of the hollow body, in which the annular union zones 102 and 104, predisposed for permanent connection by plastic ultrasonic welding, comprise annular welding projections 18 with tapered ends, in particular with triangular meridian sections. The annular welding projections 18, present on one or more of the various portions of the hollow body, are coupled with annular surfaces 19 specially shaped to receive the annular welding projections 18 and situated on another, facing portion of the hollow body.

In more detail, the first end portion 8 exhibits, in the union zone 102, an annular welding projection 18 which corresponds to a flat annular surface 19 lying in an annular recess on the third intermediate portion 10. Further, the first end portion 8 exhibits, in the annular seal zone 101, more internally and having a smaller diameter than the union zone 102, a flat annular surface 19', corresponding with a sealing annular crushing projection 18' located on the third intermediate portion 10. The second end portion 9 exhibits, in the union zone 104, in an annular recess, a flat annular surface 19 corresponding with an annular welding zone 18 located on the third intermediate portion 10; further, the second end portion 9 exhibits, in the seal zone 103, more internal and having a smaller diameter than the union zone 104, a sealing annular crushing projection 18', corresponding with a flat annular surface 19' located on the third intermediate zone 10.

The process also includes a preliminary stage of preparation of the hydrophobic filter membranes 12 and 13, by transversal cutting of a continuous belt of material.

Figure 4:
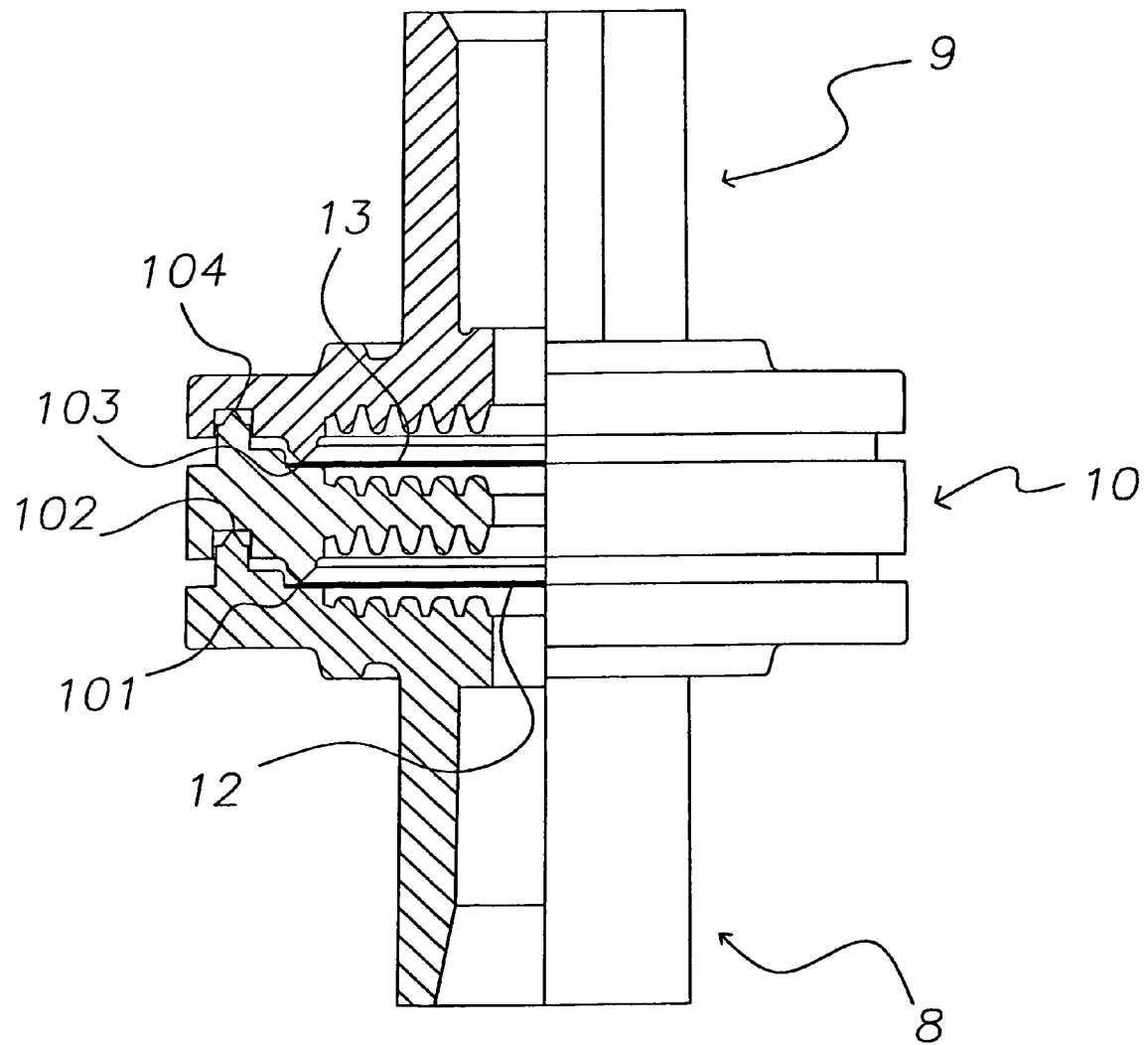
FIG. 4 is the device of FIG. 1 before the ultrasonic welding stage.
Figure 5:
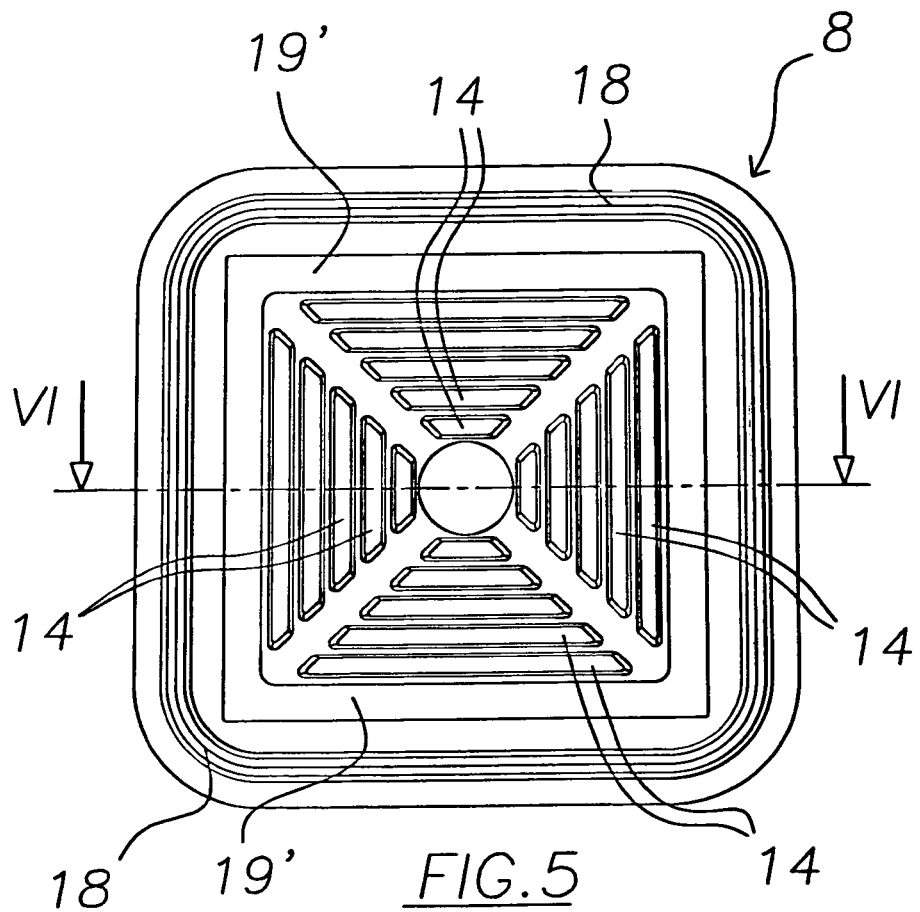
FIG. 5 is a plan view of a first portion, made of plastic, of the device of FIG. 1.
Figure 6:
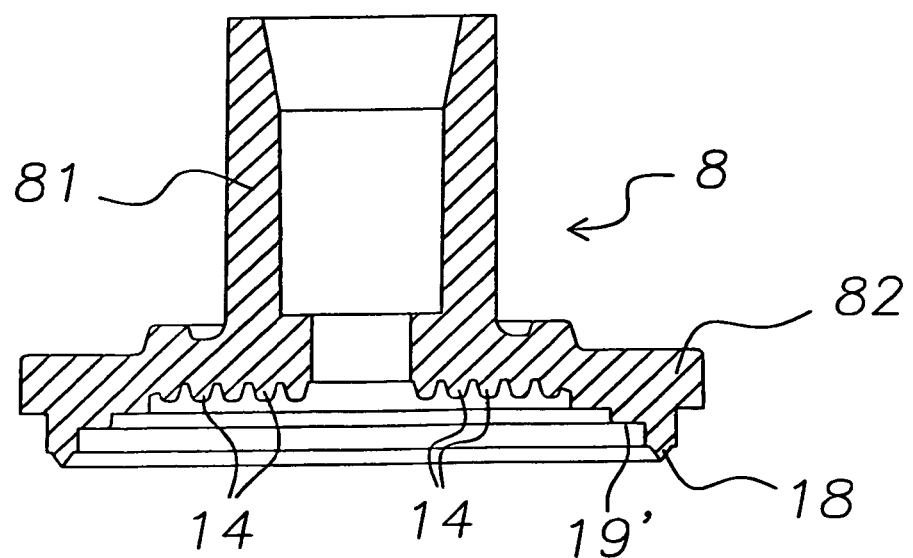
FIG. 6 is section VI-VI of FIG. 5.
Figure 8:
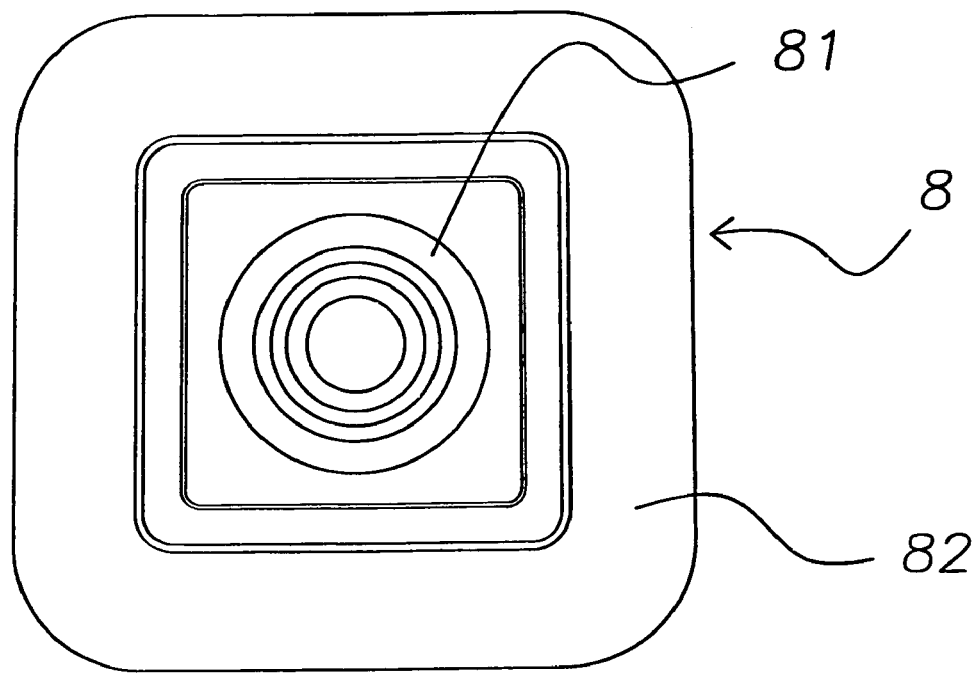
FIG. 8 is a view from below of FIG. 7.
Figure 7:
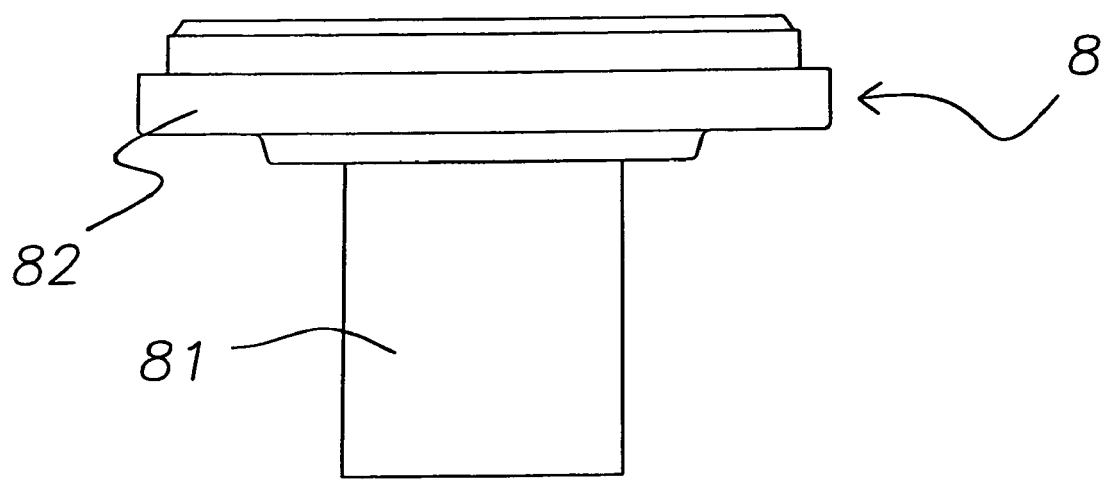
FIG. 7 is a side view of the first portion of FIG. 5.
Figure 9:
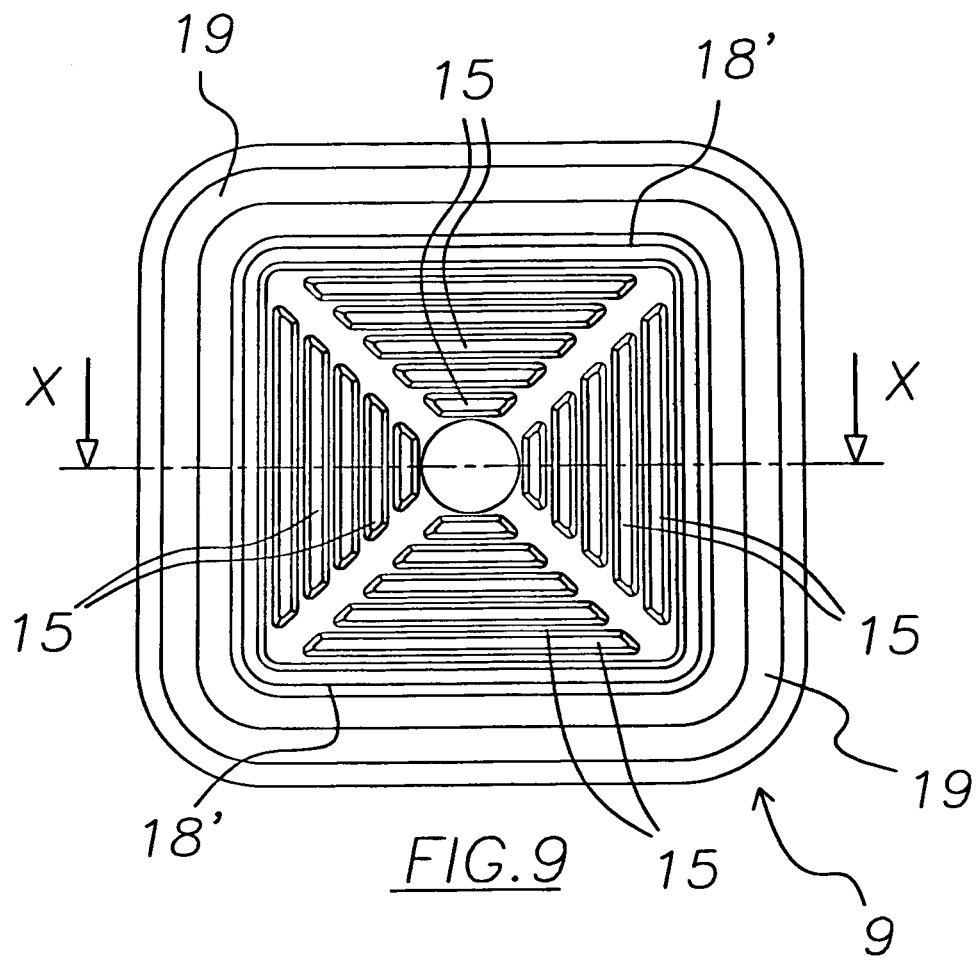
FIG. 9 is a plan view of a second portion, made of plastic, of the device of FIG. 1.
Figure 10:
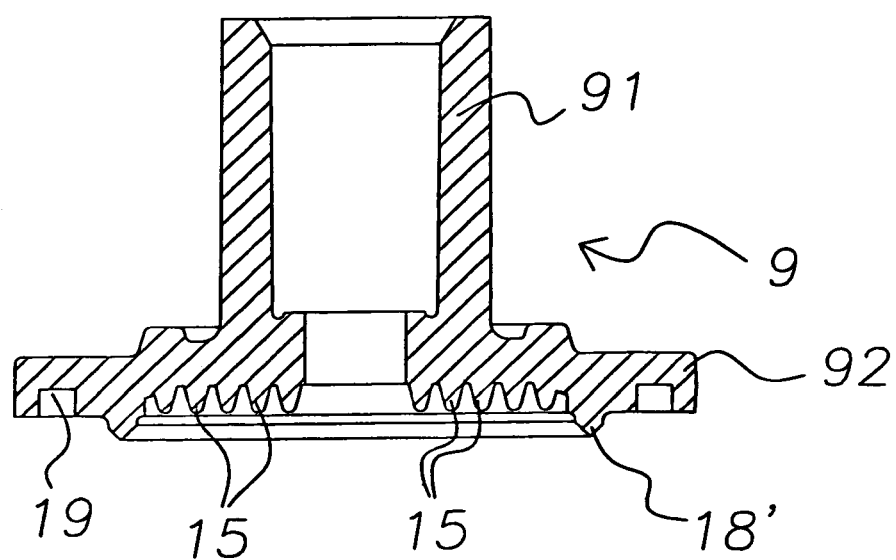
FIG. 10 is a section X-X of FIG. 9.
Figure 12:
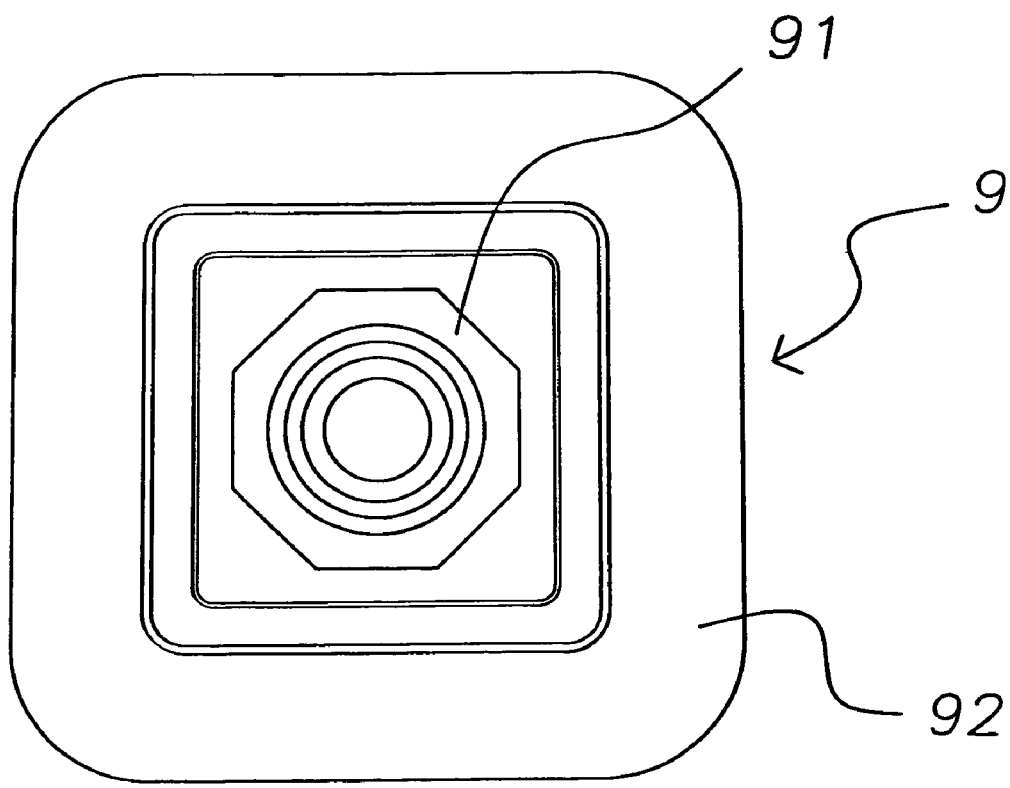
FIG. 12 is a view from below of FIG. 11.
Figure 11:
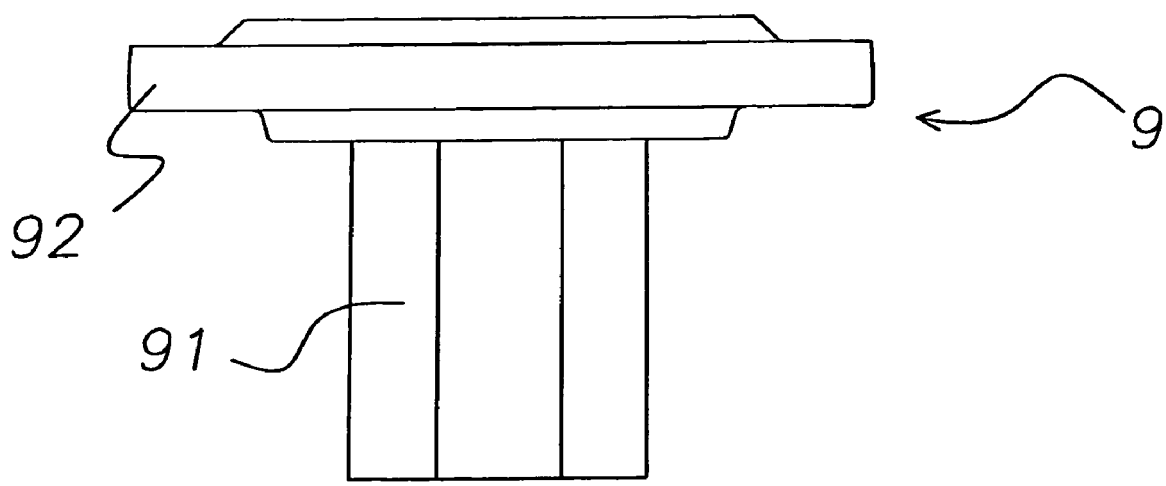
FIG. 11 is a side view of the second portion of FIG. 9.
Figure 13:
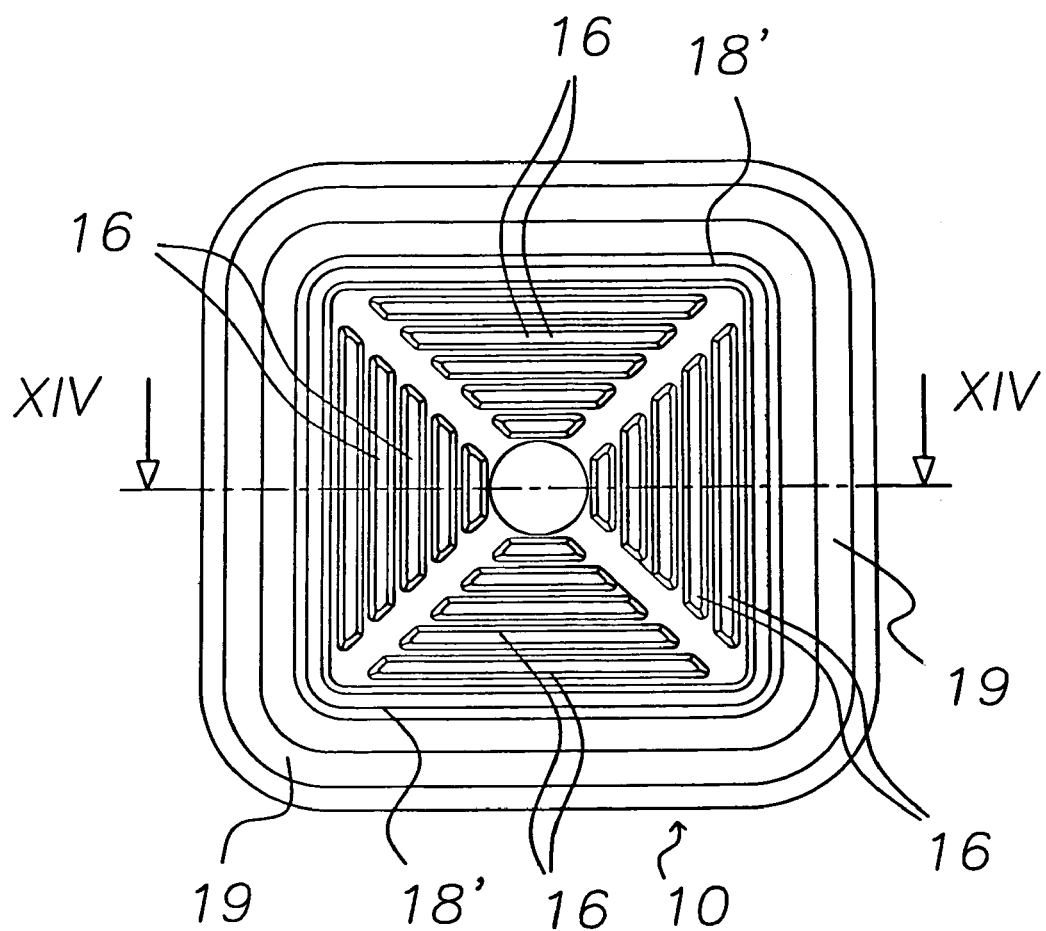
FIG. 13 is a plan view of a third portion, made of plastic, of the device of FIG. 1.
Figure 14:
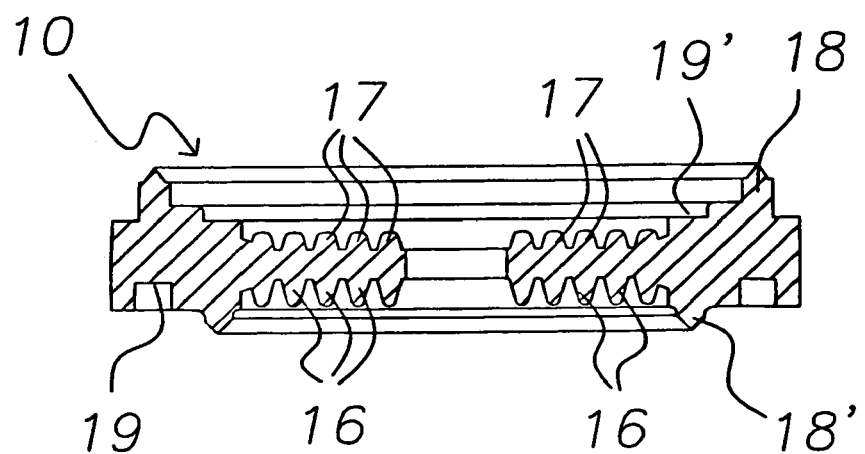
FIG. 14 is a section XIV-XIV of FIG. 13.
Figure 16:
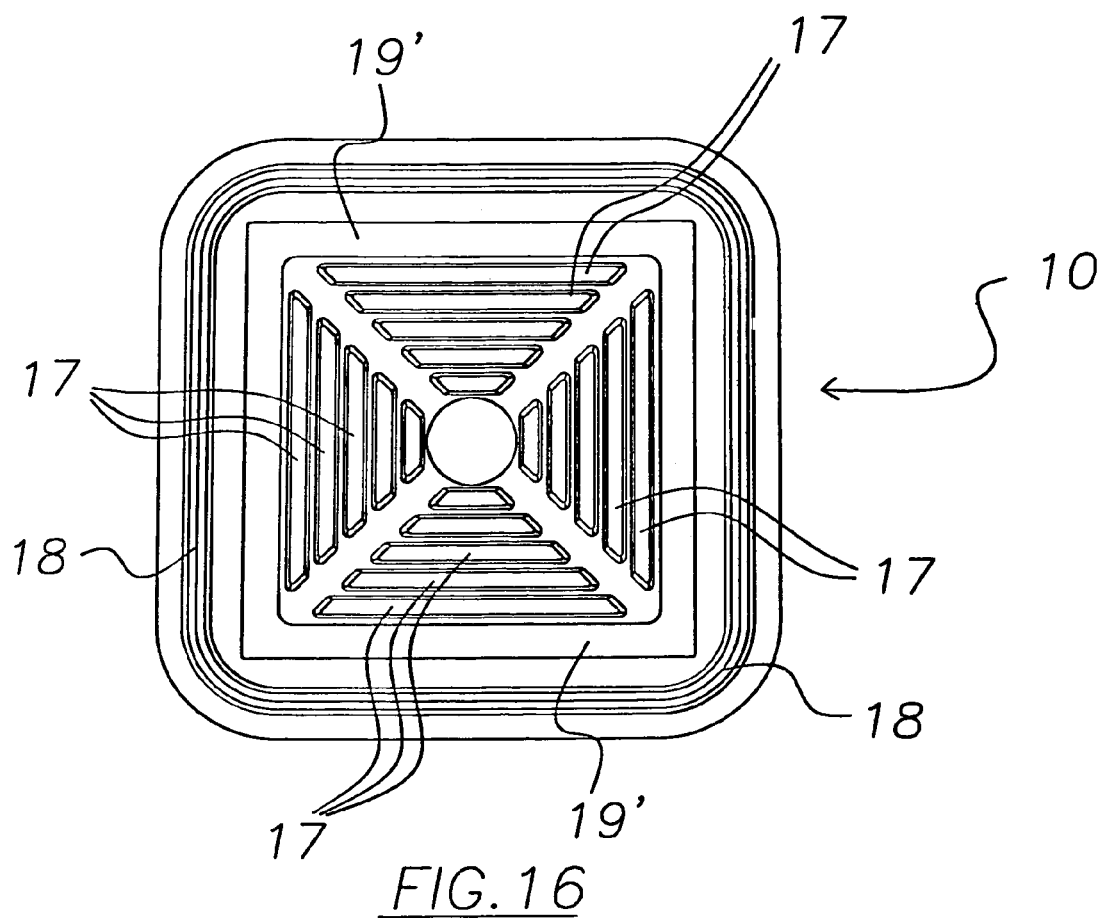
FIG. 16 is a view from below of FIG. 15.
Figure 15:
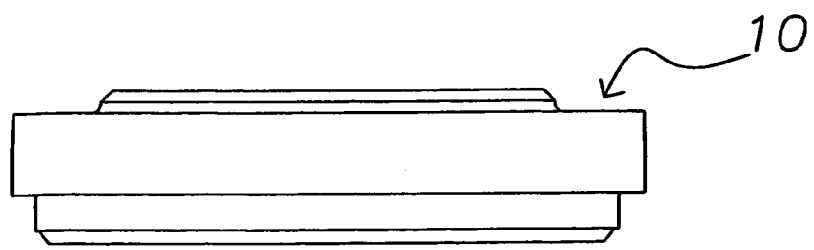
FIG. 15 is a side view of the third portion of FIG. 13.

In a subsequent stage, the three portions 8, 9 and 10 and the two filter membranes 12 and 13 are arranged in a group, with the third portion 10 interpositioned between the first and second end portions 8 and 9, the first membrane 12 being arranged transversally between the first and the third portions 8 and 10, and the second membrane 13 being arranged transversally between the third and the second portions 10 and 9, causing the annular welding projections 18 and the sealing crushing projections 18' to contact the corresponding annular surfaces 19 and 19', and interpositioning the perimeter edges of the membranes 12 and 13 between the annular seal zones 101 and 103. This grouped configuration, which precedes the welding stage, is illustrated in FIG. 4.

The process at this point includes solidly uniting the three portions 8, 9, 10 of the hollow body together, as well as the two hydrophobic protective filter membranes 12 and 13, through a simultaneous solid connection thereof, along the annular union zones 102 and 104. This simultaneous and solid connection comprises, in the illustrated embodiment, a use of ultrasonic energy which, as is known, leads to localized fusion of the annular welding projections 18. During the ultrasonic welding operation compression of the annular union zones is applied, performed with the usual machines for ultrasonic welding. The ultrasonic energy causes a partial fusion, or at least a partial softening, of the material the sealing crushing projections 18' are made of.

Figure 18:
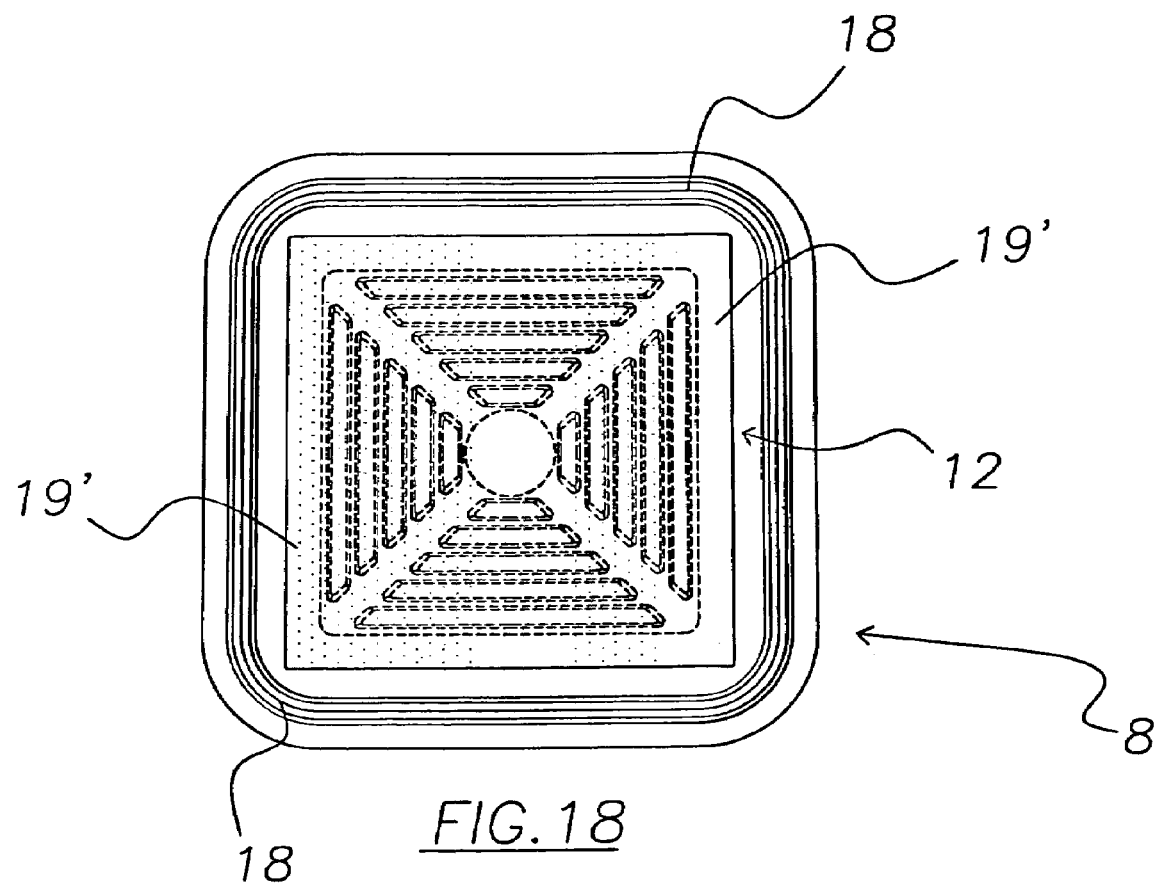
FIG. 18 is a plan view of the membrane of FIG. 13 applied on the first plastic portion of FIG. 5.
Figure 17:
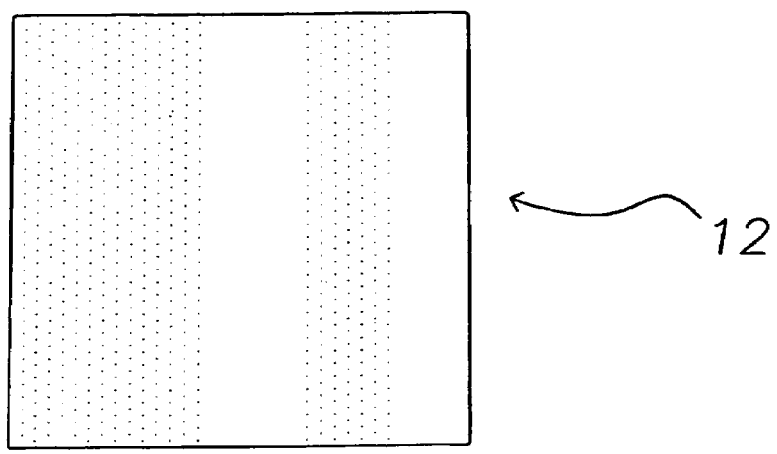
FIG. 17 is a plan view of one of the two protective membranes of the device of FIG. 1.

As shown clearly in FIGS. 17 and 18, each membrane 12 and 13. has, observed in plan view, at least one straight perimeter side. In more detail, each membrane 12 and 13. has, seen in plan view, at least a first pair of opposite perimeter sides which are parallel one to another. Each membrane 12 and 13 has, seen in plan view, a second pair of opposite perimeter sides, and in even more detail, each membrane 12 and 13 has, once more seen in plan view, a rectangular shape, which, more specifically, in the illustrated embodiment is square.

At least the two annular seal zones 101 and 103 prevalently follow the shape of the liquid-sealed membrane perimeter zone, and include rounded zones at the corners, to avoid creating union zones with live edges.

The annular union zones 102 and 104, which are arranged coaxially and more peripherally with respect to the annular seal zones 101 and 103, are more or less of the same shape, but wider, as the annular seal zones 101 and 103. In the illustrated embodiment, the annular union zones 102 and 104 have a rectangular shape, in fact are square, and have rounded corners.

In further embodiments which are not illustrated, it would be possible to use membranes having, in plan view, a polygonal shape which is different to what is described above, for example a non-equilateral rectangular shape, or a non-rectangular quadrilateral shape, or a regular polygon with more than four sides, and so on. It would also be possible to use membranes having a shape which is close to a square shape, but having sides which are not straight but rather slightly curved, with non-live but rounded edges.

All the membrane shapes described here have in common the fact of the presence of at least one perimeter side, having a curvature diameter which is greater than the lateral dimension of the membrane, the lateral dimension being considered in a perpendicular direction to the side itself. Where the perimeter side is straight, the corresponding diameter of curvature can be considered, from a purely mathematical point of view, to be of an infinite length, and thus, from a practical point of view, without doubt longer than the lateral dimension of the membrane.

The square shape, and the shapes described above, which all include at least one straight or nearly straight perimeter side, have, with respect to the usual circular shape, the advantage of offering a greater active membrane surface, in conditions of a same lateral dimension, with a consequent reduction in the drop of pressure and a better transmission of the pressure signal across the device, without losing any efficiency as far as the protective function is concerned. Further, by using membranes with at least one straight or nearly-straight perimeter side, membranes can be produced by a transversal cutting of a continuous tape, with a considerable ensuing reduction, possibly even a complete elimination, of waste of material. A further advantage of the above-described device, with a non-circular peripheral shape, is that the operator can grip the device more easily and handle it more comfortably.

In more general terms, the above-described advantages can be obtained by using a membrane having a plan shape delimited by a determined perimeter border, in which the circle of maximum possible diameter within the border has a total area which is smaller than the area of the membrane; in other words, the membrane is larger than the maximum diameter circle that can be drawn within it.

Figure 19:
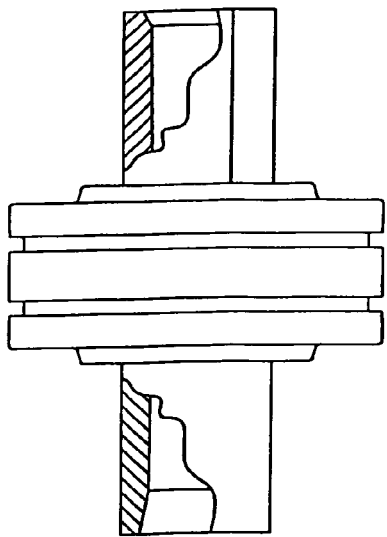
Figure 20:
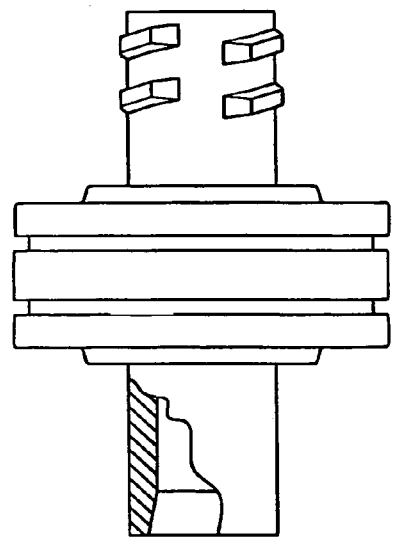
Figure 21:
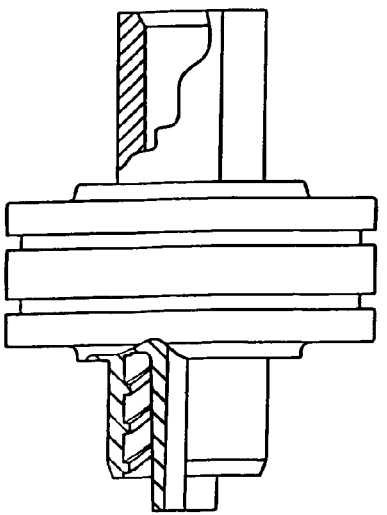
Figure 22:
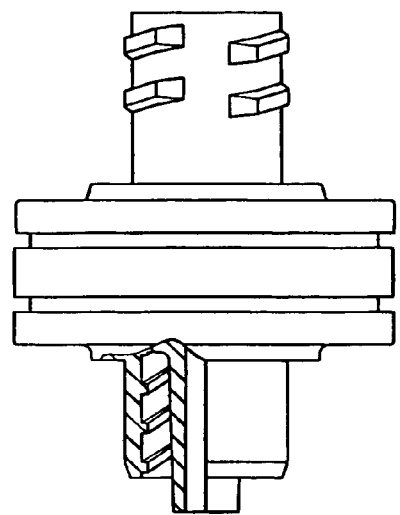

In figures from 19 to 22, four different embodiments of the double-membrane protection device of the invention are illustrated, which differ among themselves in the tubular connections: the first device (FIG. 19) exhibits two smooth connectors, for coupling to the tubes by force-fitting and gluing; the second device (FIG. 20) exhibits a smooth connector and a female Luer connector; the third device (FIG. 21) exhibits a smooth connector and a male Luer connector; the fourth device (FIG. 22) exhibits a female Luer connector and a male Luer connector.

In the embodiment illustrated in FIG. 23, a protection device 1, comprises a single hydrophobic protective membrane 12', having a plan shape which is the same as what is described above, i.e. with one or more straight perimeter sides, or nearly so, or, in more general terms, having a surface areas which is greater than a maximum circle which can be drawn therein. In this case the third intermediate portion is absent, and the only protective membrane 12' is arranged transversally between the first and the second end portions 8' and 9'.

Figure 1:
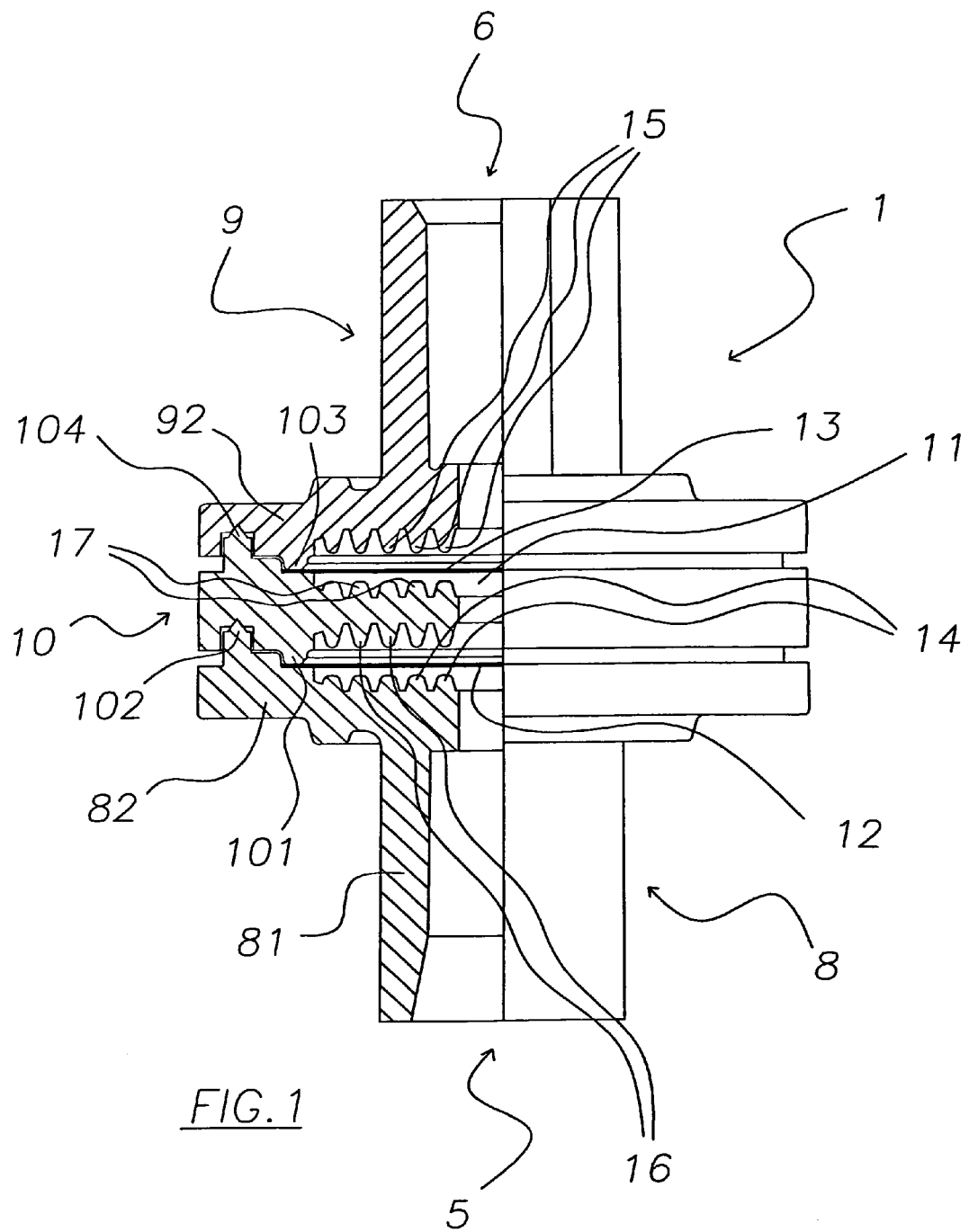
FIG. 1 is a partially-sectioned view of a device made according to the present invention.

In the first-described, and illustrated device in figures from 1 to 18, the two end portions 8 and 9 are already set up and structured to be directly couplable to each other, with the interpositioning of a single filter membrane. Therefore, in FIG. 1' of FIG. 23, the two portions 8' and 9' of the hollow body are identical to the two end portions 8 and 9 or the device 1 of figures from 1 to 18, and the filter membrane 12' is identical to the filter membrane 12 or 13.

The device 1, of FIG. 23, having a single membrane, has the advantage of providing efficient transmission of the pressure, in terms of parity of lateral dimensions, and easy grip and handling.

The invention claimed is:

1. A transduction-protection device, comprising:
a hollow body defining an internal cavity, said hollow body having:
a first end portion having a first tubular connector;
a second end portion, opposite said first end portion, said second end portion having a second tubular connector being in fluid communication with said first tubular connector through said internal cavity;
said first and second end portions being connected to each other via a third intermediate portion;
said third intermediate portion being connected between said first end portion and said second end portion, a first side of said third intermediate portion being coupled to said first end portion along at least a first union zone, a second side of said third intermediate portion configured opposite to said first side, said second side being coupled to said second end portion along at least a second union zone, said third intermediate portion having an empty central opening for transferring a pressure from the first end portion to the second end portion without significant losses of head;
a first filter membrane configured in said internal cavity of said hollow body, said first filter membrane defining a first gas-permeable anti-contamination barrier arranged transversally between said first end portion and said third intermediate portion; and
a second filter membrane configured in said internal cavity of said hollow body, said second filter membrane defining a second gas-permeable anti-contamination barrier arranged transversally between said second end portion and said third intermediate portion.

2. The device of claim 1, wherein said third intermediate portion is plate-shaped.

3. The device of claim 1, wherein said third intermediate portion comprises a single piece.

4. The device of claim 1, wherein said third intermediate portion is comprises a rigid material.

5. The device of claim 1, wherein said third intermediate portion is integrally molded in a plastic material.

6. The device of claim 1, wherein said first union zone and said second union zone are permanent coupling zones.

7. The device of claim 1, wherein said first union zone and said second union zone comprise ultrasonic welded zones.

8. The device of claim 1, wherein:
said first end portion has a first internal surface delimiting said internal cavity and facing said first membrane;
said second end portion has a second internal surface delimiting said internal cavity and facing said second membrane; and
said third intermediate portion has first and second internal surfaces delimiting said internal cavity;
said device further comprising:
a first plurality of reliefs emerging from said first internal surface of the first end portion, said first plurality of reliefs defining a first striker surface for said first membrane;
a second plurality of reliefs emerging from said second internal surface of the second end portion, said second plurality of reliefs defining a second striker surface for said second membrane;
a third plurality of reliefs emerging from said first internal surface of the third intermediate portion, said first internal surface of the third intermediate portion facing said first membrane, said third plurality of reliefs defining a third-striker surface for said first membrane; and
a fourth plurality of reliefs emerging from said second internal surface of the third intermediate portion, said second internal surface of the third intermediate portion facing the second membrane, said fourth plurality of reliefs defining a fourth striker surface for said second membrane.

9. The device of claim 8, wherein said first, second, third, and fourth pluralities of reliefs include ribs arranged tangentially with reference to a longitudinal axis of said hollow body, said ribs defining a plurality of tangential channels, said tangential channels communicating with a central zone of said internal cavity through one or more radial channels defined by said first, second, third, and fourth pluralities of reliefs.

10. The device of claim 1, wherein said first union zone and said second union zone are annular.

11. The device of claim 1, wherein said first membrane and said second membrane are at least partially facing one another.

12. The device of claim 1, comprising at least a first annular seal zone and a second annular seal zone, said first annular seal zone being configured at a perimeter edge of said first membrane, and said second annular seal zone being configured at a perimeter edge of said second membrane.

13. The device of claim 12, wherein said first union zone and said second union zone have radial dimensions of a greater size than radial dimensions of said first annular seal zone and said second annular seal zone.

14. The device of claim 1, wherein said first membrane and said second membrane each have at least one straight perimeter side.

15. The device of claim 14, wherein said first membrane and said second membrane each have at least a first pair of perimeter sides configured opposite and parallel to one another.

16. The device of claim 15, wherein said first membrane and said second membrane each have at least a second pair of perimeter sides configured opposite and parallel to one another.

17. The device of claim 16, wherein said first membrane and said second membrane each exhibit a rectangular shape.

18. The device of claim 12, wherein said first annular seal zone and said second annular seal zone each include at least two joined adjacent sides having a rounded corner.

19. The device of claim 18, wherein said first annular seal zone and said second annular seal zone each include a substantially rectangular shape having rounded corners.

20. A transduction-protection device, comprising:
a hollow body defining an internal cavity, said hollow body having:
a first end portion having a first tubular connector;
a second end portion, opposite said first end portion, said second end portion having a second tubular connector being in fluid communication with said first tubular connector through said internal cavity;
said first and second end portions being connected to each other via a third intermediate portion;
said third intermediate portion being connected between said first end portion and said second end portion, a first side of said third intermediate portion being coupled to said first end portion along at least a first union zone, a second side of said third intermediate portion configured opposite to said first side, said second side being coupled to said second end portion along at least a second union zone, said third intermediate portion being plate-shaped for transferring a pressure from the first end portion to the second end portion without significant losses of head;
a first filter membrane configured in said internal cavity of said hollow body, said first filter membrane defining a first gas-permeable anti-contamination barrier arranged transversally between said first end portion and said third intermediate portion; and
a second filter membrane configured in said internal cavity of said hollow body, said second filter membrane defining a second gas-permeable anti-contamination barrier arranged transversally between said second end portion and said third intermediate portion.

* * * * *

UNITED STATES PATENT AND TRADEMARK OFFICE
CERTIFICATE OF CORRECTION

PATENT NO.        : 7,621,983 B2                                          Page 1 of 1
APPLICATION NO.   : 11/635520
DATED             : November 24, 2009
INVENTOR(S)       : Roberto Neri It is certified that error appears in the above-identified patent and that said Letters Patent is hereby corrected as shown below:

In claim 4, column 8, line 65, "portion is comprises" should read --portion comprises--.

In claim 8, column 9, line 27, "third-striker" should read --third striker--.

Signed and Sealed this

Ninth Day of February, 2010

David J. Kappos
*Director of the United States Patent and Trademark Office*